US008473028B2

(12) United States Patent
Mitsouras et al.

(10) Patent No.: US 8,473,028 B2
(45) Date of Patent: Jun. 25, 2013

(54) K-SPACE SAMPLE DENSITY COMPENSATION FOR MAGNETIC RESONANCE IMAGE RECONSTRUCTION

(75) Inventors: Dimitrios Mitsouras, Brookline, MA (US); Frank J. Rybicki, Sudbury, MA (US); Robert V. Mulkern, Waban, MA (US)

(73) Assignees: The Brigham and Women's Hospital, Boston, MA (US); Children's Medical Center Corporation, Boston, MA (US)

(*) Notice: Subject to any disclaimer, the term of this patent is extended or adjusted under 35 U.S.C. 154(b) by 378 days.

(21) Appl. No.: 12/743,030

(22) PCT Filed: Nov. 21, 2008

(86) PCT No.: PCT/US2008/084397
§ 371 (c)(1),
(2), (4) Date: Aug. 5, 2010

(87) PCT Pub. No.: WO2009/067691
PCT Pub. Date: May 28, 2009

(65) Prior Publication Data
US 2010/0305424 A1 Dec. 2, 2010

Related U.S. Application Data
(60) Provisional application No. 60/989,606, filed on Nov. 21, 2007.

(51) Int. Cl.
*A61B 5/055* (2006.01)
*G06K 9/00* (2006.01)
(52) U.S. Cl.
USPC .......................... 600/410; 382/128
(58) Field of Classification Search
None
See application file for complete search history.

(56) References Cited

U.S. PATENT DOCUMENTS

| 6,043,652 | A * | 3/2000 | Liu ........................... 324/309 |
| 6,748,098 | B1 | 6/2004 | Rosenfeld |
| 6,784,664 | B2 * | 8/2004 | Liang et al. .................. 324/309 |
| 7,076,091 | B2 * | 7/2006 | Rosenfeld ..................... 382/131 |
| 7,903,858 | B2 * | 3/2011 | Chang et al. .................. 382/131 |
| 8,170,311 | B2 * | 5/2012 | Ying ............................ 382/128 |
| 2005/0058368 | A1 | 3/2005 | Moriguchi et al. |

OTHER PUBLICATIONS

International Search Report and Written Opinion corresponding to PCT/US2008/084397 under date of mailing of Apr. 9, 2009.
Afacan, O., et al., "Comparing MR Imaging Properties of Spiral Trajectories Using the Singular Spectrum of the Analytical Fourier Basis Cross-Correlation Matrix." IEEE, 2007, pp. 1080-1083.
Mitsouras, D., et al., "Basis function cross-correlations for robust k-space sample density compensation, with application to the design of radiofrequency excitations." Magnetic Resonance in Medicine, 2007, vol. 57, pp. 338-352.

* cited by examiner

*Primary Examiner* — Long V. Le
*Assistant Examiner* — Angela M Hoffa
(74) *Attorney, Agent, or Firm* — Quarles & Brady, LLP

(57) ABSTRACT

The present invention provides a method for producing density-compensated MR images having improved signal-to-noise ratio and with reduced computational burden. The method includes sampling MR data using a rotationally symmetric acquisition trajectory, generating a cross-correlation matrix, and applying a discreet Fourier transform (DFT) to the acquired MR data and the cross correlation matrix. The method further includes employing the transformed MR data and transformed cross-correlation matrix in a linear system to produce a set of density-compensated transformed MR data, which may transformed into density compensated MR data by application of an inverse DFT. The density compensated MR data may be reconstructed by a variety of techniques to produce density compensated images.

20 Claims, 4 Drawing Sheets

K-SPACE SAMPLE DENSITY COMPENSATION FOR MAGNETIC RESONANCE IMAGE RECONSTRUCTION

REFERENCE TO RELATED APPLICATIONS

This application is based on provisional application Ser. No. 60/989,606, filed Nov. 21, 2007, and entitled "K-SPACE SAMPLE DENSITY COMPENSATION FOR MAGNETIC RESONANCE IMAGE RECONSTRUCTION," and claims the benefit thereof.

STATEMENT REGARDING FEDERALLY SPONSORED RESEARCH

This invention was made with United States government support awarded by the following agency: NIH grant K23-EB00882. The United States has certain rights in this invention.

BACKGROUND OF THE INVENTION

The field of the invention is nuclear magnetic resonance imaging (MRI) methods and systems. More particularly, the invention relates to the reconstruction of images from acquired MR data that samples k-space in a non-uniform manner.

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the plane orthogonal to the main polarizing field (generally designated the x-y plane) and that is near the Larmor frequency, the net aligned moment, $M_z$, may be rotated, or "tipped", into the x-y plane to produce a net transverse magnetic moment $M_t$. A signal emitted by the excited nuclei or "spins" may be received after the excitation signal $B_1$ is terminated, and may be processed to form an image.

When utilizing these "MR" signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

The MR signals acquired with an MRI system are signal samples of the subject of the examination in Fourier space, or what is often referred to in the art as "k-space". Each MR measurement cycle, or pulse sequence, typically samples a portion of k-space along a sampling trajectory characteristic of that pulse sequence. Most pulse sequences sample k-space in a raster scan-like pattern sometimes referred to as a "spin-warp", a "Fourier", a "rectilinear" or a "Cartesian" scan. The spin-warp scan technique is discussed in an article entitled "Spin-Warp MR Imaging and Applications to Human Whole-Body Imaging" by W. A. Edelstein et al., Physics in Medicine and Biology, Vol. 25, pp. 751-756 (1980). It employs a variable amplitude phase encoding magnetic field gradient pulse prior to the acquisition of MR spin-echo signals to phase encode spatial information in the direction of this gradient. In a two-dimensional implementation (2DFT), for example, spatial information is encoded in one direction by applying a phase encoding gradient ($G_y$) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($\Delta G_y$) in the sequence of measurement cycles, or "views" that are acquired during the scan to produce a set of k-space MR data from which an entire image can be reconstructed.

There are many other k-space sampling patterns used by MRI systems These include "radial", or "projection reconstruction" scans in which k-space is sampled as a set of radial sampling trajectories extending from the center of k-space as described, for example, in U.S. Pat. No. 6,954,067. The pulse sequences for a radial scan are characterized by the lack of a phase encoding gradient and the presence of a readout gradient that changes direction from one pulse sequence view to the next. There are also many k-space sampling methods that are closely related to the radial scan and that sample along a curved k-space sampling trajectory rather than the straight line radial trajectory. Such pulse sequences are described, for example, in "Fast Three Dimensional Sodium Imaging", MRM, 37:706-715, 1997 by F. E. Boada, et al. and in "Rapid 3° D. PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia.

An image is reconstructed from the acquired k-space data by transforming the k-space data set to an image space data set. There are many different methods for performing this task and the method used is often determined by the technique used to acquire the k-space data. With a Cartesian grid of k-space data that results from a 2D or 3D spin-warp acquisition, for example, the most common reconstruction method used is an inverse Fourier transformation ("2DFT" or "3DFT") along each of the 2 or 3 axes of the data set. With a radial k-space data set and its variations, the most common reconstruction method includes "regridding" the k-space samples to create a Cartesian grid of k-space samples and then perform a 2DFT or 3DFT on the regridded k-space data set. In the alternative, a radial k-space data set can also be transformed to Radon space by performing a 1DFT of each radial projection view and then transforming the Radon space data set to image space by performing a filtered backprojection.

Reconstructing images from k-space samples acquired using other non-Cartesian trajectories can be more difficult. The acquired MR samples do not provide independent information about an imaged object over a selected field-of-view (FOV) and must therefore be weighted to account for non-uniform sampling density. This weighting process is referred to as density compensation and images reconstructed from unweighted MR data will include inaccuracies and will not properly represent an imaged object.

A traditional method of performing density compensation involves multiplying a density compensation function (DCF), which ideally accounts for the Jacobian in the Fourier transform integral relationship, with samples acquired using non- Cartesian acquisition trajectories. However, computing the Jacobian determinant requires the existence of an analytical transformation for the given trajectory to a uniformly unit-space coordinate system that may not be available for trajectories used in MRI. It is possible to numerically evaluate the DCF by defining area elements associated with each sample to mimic the Jacobian and by implementing goal-based optimization of the point-spread function (PSF) defined by the Fourier expansion of the DCF. However, numerical methods do not always adequately evaluate the DCF, as the optimization of the PSF relies on iterative refinement methods that do not guarantee convergence.

Other methods for performing density compensation employ linear systems to model the imaging or resampling problem. These methods often include the direct inversion of large and dense matrices, a computationally expensive process that is especially problematic when producing large MR images. Computational burden may be reduced by employing iterative linear system solvers and stopping criteria or by employing heuristic simplifications such as truncation or approximation. However, these simplification methods do not provide exact density compensation and generally lead to MR images having reduced accuracy.

It would therefore be desirable to provide a method for performing an accurate density compensation on MR data acquired using non-uniform acquisition trajectories. Such a method would reduce reconstruction errors when producing MR images and provide improved signal-to-noise ratio (SNR).

SUMMARY OF THE INVENTION

The present invention overcomes the limitations of traditional methods by providing a method for producing density-compensated magnetic resonance (MR) images with a magnetic resonance imaging (MRI) system. The method includes acquiring MR data using a rotationally symmetric acquisition trajectory, generating a cross-correlation matrix that describes the interactions (i.e., co-dependence) between the acquired k-space MR data, and applying a discreet Fourier transform (DFT) to the acquired MR data and the cross-correlation matrix. The method further includes computing a set of density-compensated, transformed MR data from the transformed cross-correlation matrix and transformed MR data and applying an inverse DFT to the density-compensated, transformed MR data to produce a set of density-compensated MR data. The method further includes performing image reconstruction on the density-compensated MR data to produce a density-compensated MR image.

The present invention further provides a method for improving the SNR of density-compensated MR images by employing a scaling factor to constrain the amplitudes of the density-compensated MR data.

Various other features of the present invention will be made apparent from the following detailed description and the drawings.

DESCRIPTION OF THE INVENTION

Figure 1:
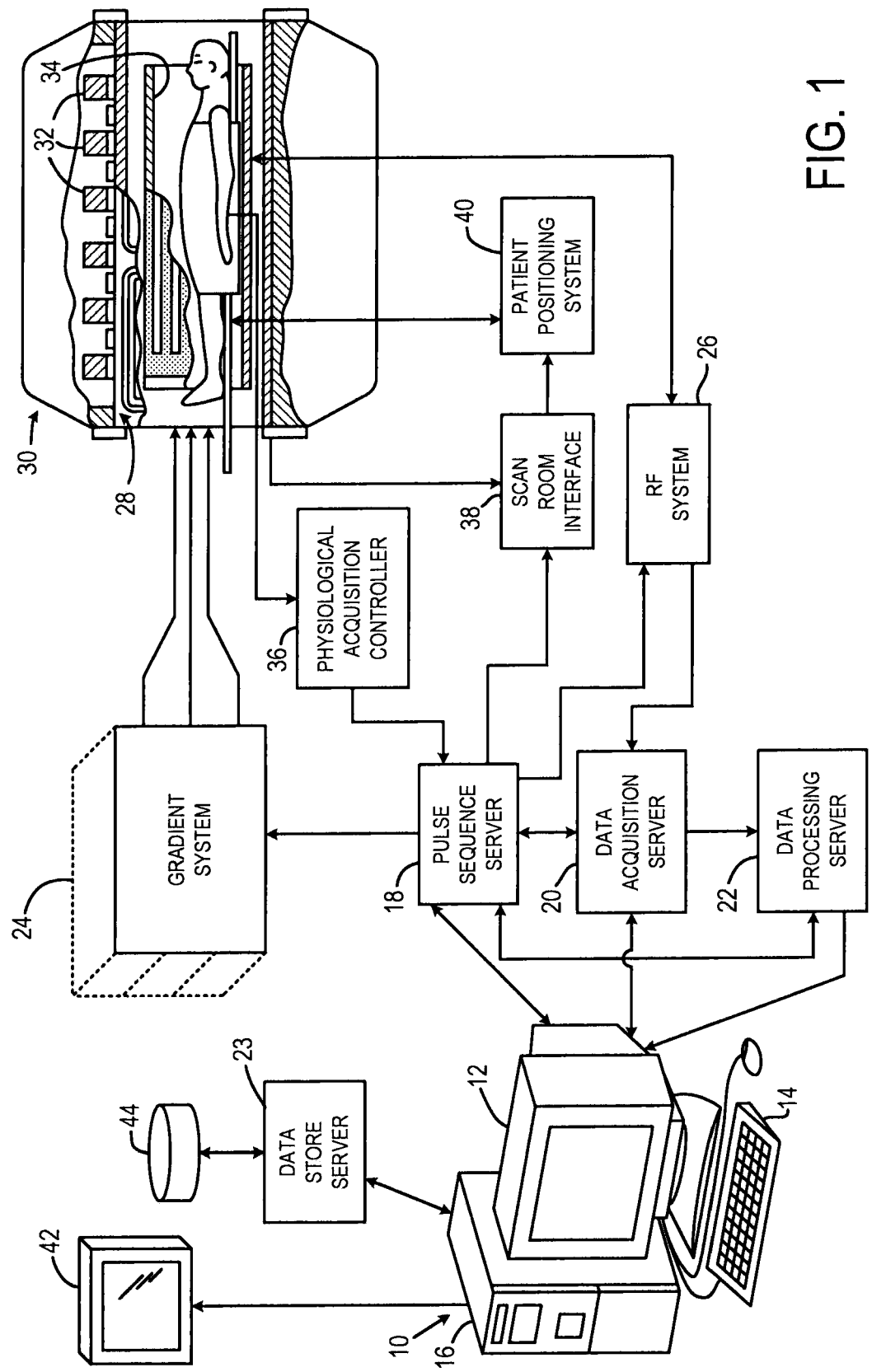
FIG. 1 is a block diagram of an MRI system that employs the present invention.

Referring to FIG. 1, the present invention is employed in an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to four servers including a pulse sequence server 18, a data acquisition server 20, a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$ and $G_z$ used for position encoding MR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive MR signals detected by the RF coil 34 or a separate local coil (not shown in FIG. 1) are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays (not shown in FIG. 1).

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi=\tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during prescans, MR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process MR signals used to detect the arrival of contrast agent in an MRA scan. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example, Fourier transformation of raw k-space MR data to produce two or three-dimensional images, the application of filters to a reconstructed image, the performance of a backprojection image reconstruction of acquired MR data; the calculation of functional MR images, the calculation of motion or flow images, and the like.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
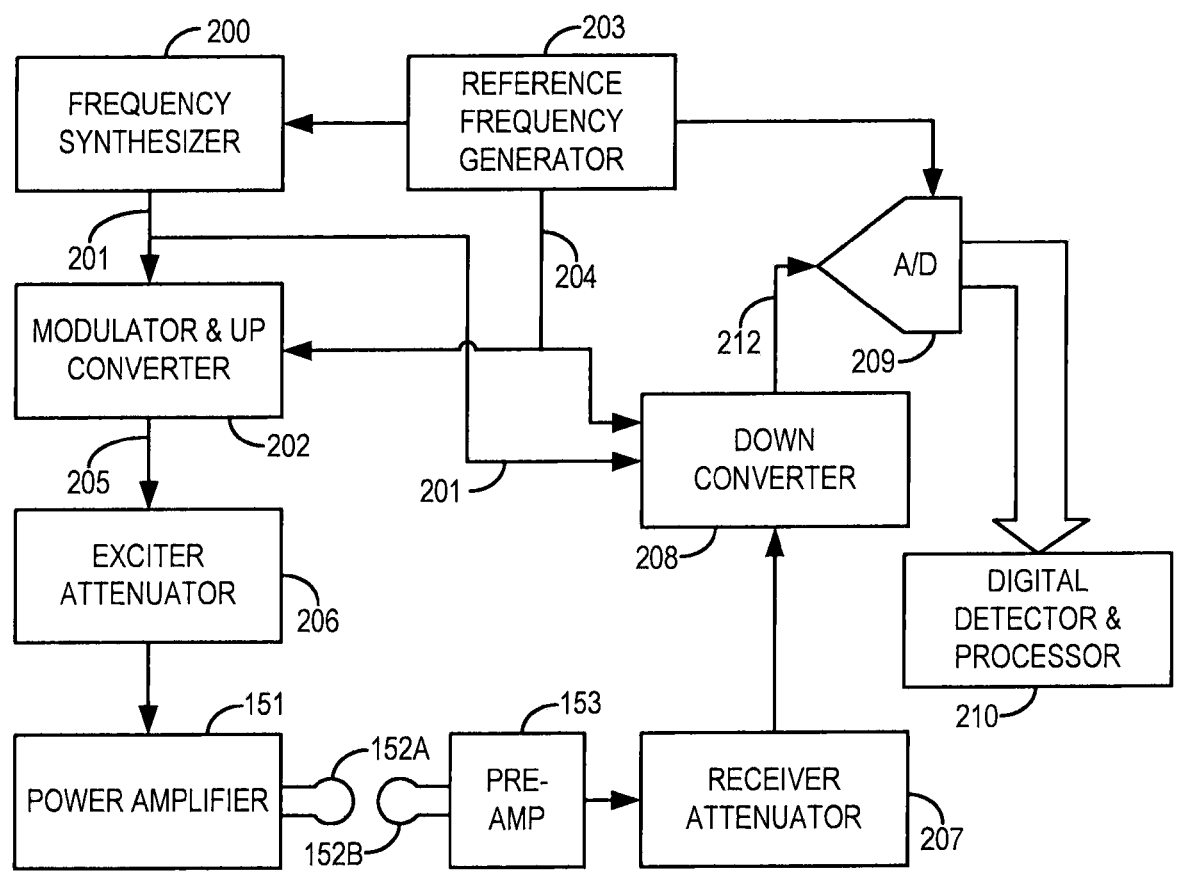
FIG. 2 is a block diagram of an RF system that forms part of the MRI system of FIG. 1.

As shown in FIG. 1, the RF system 26 may be connected to the whole body RF coil 34, or as shown in FIG. 2, a transmitter section of the RF system 26 may connect to one RF coil 152A and its receiver section may connect to a separate RF receive coil 152B. Often, the transmitter section is connected to the whole body RF coil 34 and each receiver section is connected to a separate local coil 152B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 152A.

Referring still to FIG. 2 the signal produced by the subject is picked up by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two step process by a down converter 208 that first mixes the MR signal with the carrier signal on line 201 and then mixes the resulting difference signal with a reference signal on line 204. The down converted MR signal is applied to the input of an analog-to-digital (A/D) converter 209 that samples and digitizes the analog signal and applies it to a digital detector and signal processor 210 that produces 16-bit in-phase (I) values and 16-bit quadrature (Q) values corresponding to the received signal. The resulting stream of digitized I and Q values of the received signal are output to the data acquisition server 20. The reference signal as well as the sampling signal applied to the A/D converter 209 are produced by a reference frequency generator 203.

With the present invention, density compensation is modeled as a linear system that is based on the cross-correlation of Fourier basis functions, which typically have the form $f^j(r) = e^{-i2\pi(k^j \cdot (r)^T)}$. In this case, the two-dimensional vector $k^j \equiv (k_x^j, k_y^j)$ denotes the k-space location of a $j^{th}$ sample, the vector $r=(x,y)$ denotes spatial location, and the superscript $(.)^T$ denotes a vector transpose operation.

When MR data is acquired using non-Cartesian acquisition trajectories, for example, PROPELLER, BLADE, spiral, radial trajectories, or the like, the Fourier basis functions are non-orthogonal over a design FOV (R). Therefore, the inner product, or cross-correlation, of Fourier basis functions corresponding to sample points j and j', $f^j(r)$ and $f^{j'}(r)$ respectively, does not equal zero. This relationship is described by the following equation:

$$\langle f^j(r), f^{j'}(r) \rangle = \int_R f^j(r)(f^{j'}(r))^* dr \neq 0 \qquad \text{Eqn. 1;}$$

where the superscript $(.)^*$ denotes the Hermitian conjugate. For simplicity this cross-correlation operation, that is, $\langle f^j(r), f^{j'}(r) \rangle$, is referred to as $\psi(j,j')$. Furthermore, superscripts are used to address different function or matrices among a collection of related items and subscripts are used to index vectors and matrix elements.

The present invention provides proper density compensation by employing the linear system Ax=b, where A is a cross-correlation matrix having entries $A_{j,j'} = \psi(j, j')$, b is a matrix containing acquired MR k-space samples, which do not provide independent information about an imaged object, and x is a set of density-compensated MR data. The present invention allows a proper formulation of the density compensation problem and does not make assumptions about the imaged object, the sampling trajectory, or the point-spread function of the MRI system. Furthermore, the matrix A can be determined analytically for square, rectangular, and disk-shaped FOVs, allowing the density compensation linear system to be analyzed without discretization or simplification. For example, for spiral, PROPELLER, or radial acquisition trajectories conforming to a disk-shaped FOV, the cross-correlation matrix A can be described using the following function:

$$\psi(j, j') = \begin{cases} \pi/4 & \text{when } j = j' \\ \dfrac{1}{2\Delta q(j, j')} J_1(\pi \Delta q(j, j')) & \text{when } j \neq j'; \end{cases} \quad \text{Eqn. 2}$$

where $\Delta q(j,j') = \sqrt{(k_x^j - k_x^{j'})^2 + (k_y^j - k_y^{j'})^2}$ and $J_1(\cdot)$ is the Bessel function of the first kind.

Figure 3:
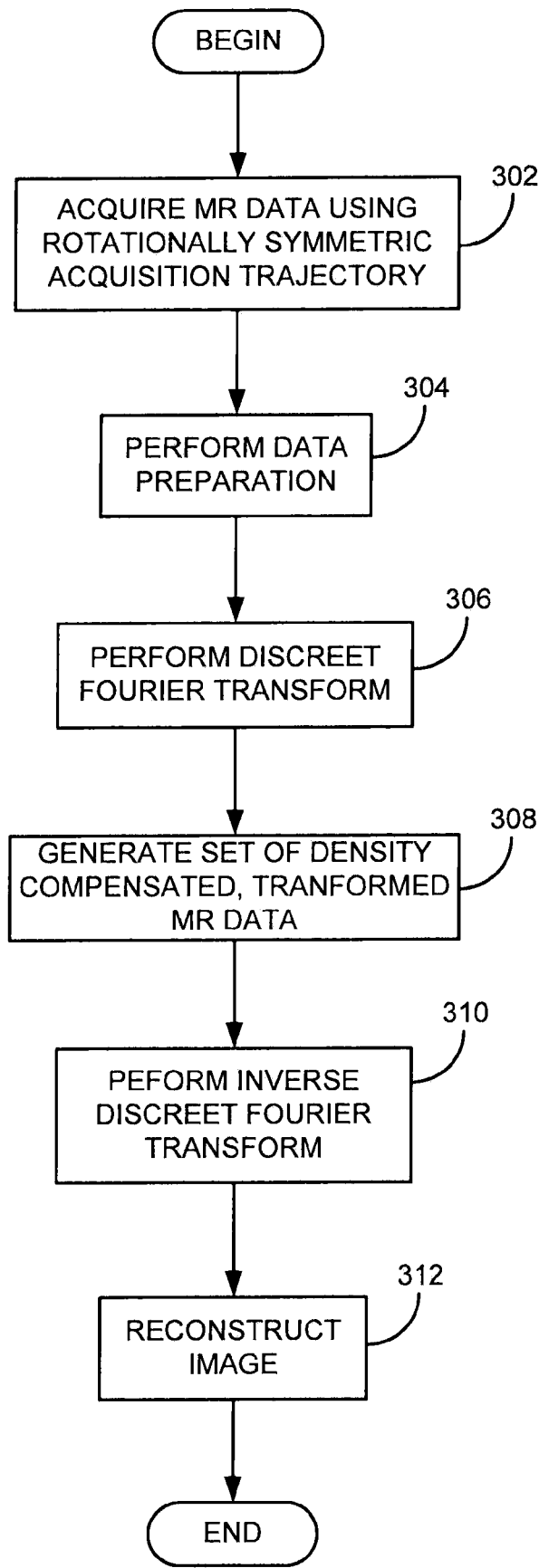
FIG. 3 is a flowchart setting forth the steps of producing density-compensated MR images in accordance with the present invention.
Figure 4:
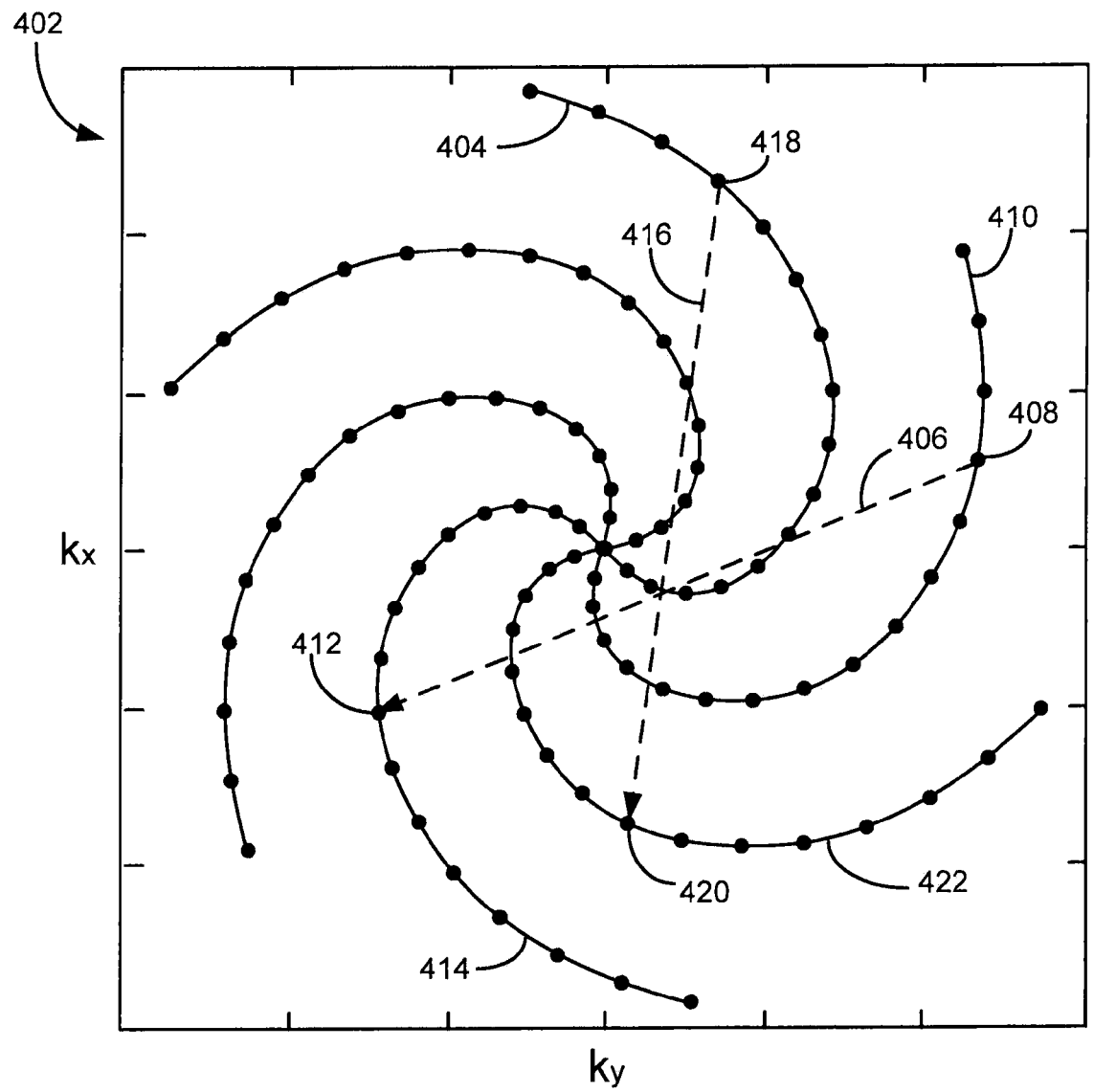
FIG. 4 is a schematic showing a rotationally symmetric acquisition trajectory in accordance with the present invention.

Referring to FIGS. 3 and 4, the above-mentioned MRI system and linear system Ax=b may be employed to produce density-compensated images of a subject. The process begins at process block 302 by acquiring MR data using a rotationally symmetric sampling trajectory that includes n segments, or "interleaves", that include m samples. It is contemplated that a variety of rotationally symmetric acquisition trajectories such as PROPELLER, BLADE, concentric rings, spiral, radial trajectories, and the like may be used. For example, a spiral sampling trajectory 402 is illustrated in FIG. 4 that includes six interleaves that each have a equal number of samples, which are denoted here by dots. The interleaves may be numbered sequentially in a clockwise fashion from one to n, where a first interleave, for example, spiral interleave 404, is chosen arbitrarily. The acquired MR data may be loaded onto n vectors $b^\alpha$, which together correspond to the matrix b and where a denotes the interleave that a sample is acquired on. For example, samples from the first spiral interleave 404 would be stored on vector $b^1$.

Referring again to FIG. 3, at process block 304, a data preparation process is performed to arrange the data in k-space locations such that the ensemble of data can be divided into n sets of data where each set is a symmetrical copy of a set arbitrarily named set one. It is contemplated that this may be achieved by generating the nm-by-nm cross correlation matrix A. If the cross-correlation between samples in an interleave-α and an interleave-β are defined by the m-by-m block-matrix $C^{\alpha,\beta}$, then the cross-correlation matrix A has the following form:

$$A = \begin{bmatrix} C^{1,1} & \cdots & C^{n,1} \\ \vdots & \ddots & \vdots \\ C^{1,n} & \cdots & C^{n,n} \end{bmatrix}. \quad \text{Eqn. 3}$$

Without further processing, it would be extremely computationally expensive to calculate density-compensated MR data with the large, dense matrix A. For example, reconstruction of a 256-by-256 MR image matrix would include the inversion of a cross-correlation matrix having $256^2$-by-$256^2$ entries. Improved computational efficiency is provided by considering the structure of the cross-correlation matrix A, which has entries that depend only on the k-space distance $\Delta q$ between samples. Therefore, because the interleaves acquired at process block 302 are rotationally symmetric, the distance between a sample j on a first interleave and a sample j' on an interleave-β is the same as the distance between the sample j on the first interleave and a sample j' on the interleave β−α+1. This relationship is described by the following equation:

$$C^{\alpha,\beta} \equiv \begin{cases} C^{1,\beta-\alpha+1} & \text{when } \beta - \alpha + 1 > 0 \\ C^{1,n+\beta-\alpha+1} & \text{otherwise.} \end{cases} \quad \text{Eqn. 4}$$

For example, referring again to FIG. 4, the distance 406 between the $j^{th}$ sample 408 on the second interleave 410 and the $j'^{th}$ sample 412 on the fourth interleave 414 is equivalent to the distance 416 between the $j^{th}$ sample 418 on the first interleave 404 to the $j'^{th}$ sample 420 on the third interleave 422. That is, $C_{j,j'}^{2,4} \equiv d_1 \equiv C_{j,j'}^{1,3}$. Recognizing the relationship between samples on rotationally symmetric interleaves, allows the matrix A to be identified as a circulant block-Toeplitz matrix having the following form:

$$A = \begin{bmatrix} C^{(1,1)} & C^{(1,n)} & C^{(1,n-1)} & \cdots & C^{(1,2)} \\ C^{(1,2)} & C^{(1,1)} & C^{(1,n)} & \cdots & C^{(1,3)} \\ \vdots & \vdots & \vdots & \ddots & \vdots \\ C^{(1,n-1)} & C^{(1,n-2)} & C^{(1,n-3)} & \cdots & C^{(1,n)} \\ C^{(1,n)} & C^{(1,n-1)} & C^{(1,n-2)} & \cdots & C^{(1,1)} \end{bmatrix}. \quad \text{Eqn. 5}$$

Furthermore, the matrix A is symmetric by construction, that is, $\psi(j,j') = \psi(j',j))$. Therefore, it can be shown that $C^{1,n} \equiv (C^{1,2})^T$ and, by collecting all such equalities, that A is symmetric when $C^{1,\alpha} = (C^{1,n-\alpha+2})^T$ for all interleaves $\alpha = ([n/2]+2)$ to $\alpha = n$. This transposition symmetry allows the cross-correlation matrix A to have the simplified form:

$$A = \begin{bmatrix} C^{1,1} & (C^{1,2})^T & \cdots & C^{1,2} \\ C^{1,2} & C^{1,1} & \cdots & C^{1,3} \\ \vdots & \vdots & \cdots & \vdots \\ C^{1,\lfloor n/2 \rfloor+1} & C^{1,\lfloor n/2 \rfloor} & \cdots & (C^{1,\lfloor n/2 \rfloor})^T \\ (C^{1,\lfloor n/2 \rfloor})^T & C^{1,\lfloor n/2 \rfloor+1} & \cdots & (C^{1,\lfloor n/2 \rfloor-1})^T \\ (C^{1,\lfloor n/2 \rfloor-1})^T & (C^{1,\lfloor n/2 \rfloor})^T & \cdots & (C^{1,\lfloor n/2 \rfloor-2})^T \\ \vdots & \vdots & \vdots & \vdots \\ (C^{1,2})^T & (C^{1,3})^T & \cdots & C^{1,1} \end{bmatrix}; \quad \text{Eqn. 6}$$

where the matrix can be described entirely by the entries in its first column of block matrices (C), as each subsequent block column is a sequential down-shift of the previous one.

Referring to FIG. 3, at process block 306, an n-point discreet Fourier transform (DFT) along the rotationally symmetric dimension is applied to the data in vectors $b^\alpha$ and the block-matrices C of the cross-correlation matrix A. This transform produces n vectors $\hat{b}$ and n block-matrices $\hat{c}$ and leads to the transformed linear system matrix $\hat{A}\hat{x} = \hat{b}$, which may be rewritten as:

$$\left( \sum_{\beta=1}^{n} W_{\alpha,\beta} C^{1,\alpha} \right) \hat{x}^\alpha = \hat{b}^\alpha; \quad \text{Eqn. 7}$$

where $W_{\alpha,\beta}$ denotes an element at the given row and column of the n-by-n normalized DFT matrix W. Application of the DFT further simplifies the linear system by block-diagonalizing the cross-correlation matrix A and transforms the linear system into a n independent m-by-m matrices that may be solved in parallel, greatly improving computational efficiency. Furthermore, these n systems, due to the transposition symmetry of matrix A, are based on only ([n/2]+1) unique m-by-m matrices. For example, producing 256-by-256 pixel MR images using a 32-interleave trajectory would include solving for a cross-correlation matrix having an original size of $256^2$-by-$256^2$. However, by acquiring only rotationally symmetric interleaves and by applying the DFT to the linear system, the 256-by-256 image may be produced using only 17 independent 2048-by-2048 matrices.

Referring still to FIG. 3, at process block 308, density compensation is performed to generate a set of density-compensated, transformed MR data. It is contemplated that this is achieved by solving the linear system of Eqn. 7 for x^. As mentioned above, the application of the DFT to the linear system produces n independent m-by-m matrices, which may be solved in parallel for greatly improved computational efficiency.

At process block 310, an n-point inverse DFT is performed on the transformed density corrected samples in the matrix x^ to produce the density-compensated samples in the matrix x. At process block 312, the density-compensated MR data is reconstructed into an MR image. Reconstruction may be performed using a variety of techniques, for example, the density-compensated MR data in x may be regridded into a Cartesian grid and reconstructed using Fourier transform reconstruction techniques. Alternately, the density-compensated MR data may be used with a non-uniform fast Fourier transform to produce a MR image.

It is recognized that the density compensation process at process block 308 provides an infinite amount of solutions to the linear system. Therefore, it is further contemplated that the present invention may provide improved SNR by employing the following modified linear system when calculating x^:

$$\left[ \begin{array}{c} \left( \sum_{\beta=1}^{n} W_{\alpha,\beta} C^{1,\alpha} \right) x^{\wedge \alpha} = b^{\wedge \alpha} \\ \lambda I_{m \times m} \end{array} \right] x^{\wedge \alpha} = \left[ \begin{array}{c} b^{\wedge \alpha} \\ 0 \end{array} \right]; \quad \text{Eqn. 8}$$

where $I_{m \times m}$ denotes an m-by-m identity matrix and $\lambda$ is a scaling factor that may be used to control that amplitude of solutions to the linear system. The modified linear system allows the amplitude of density-compensated coefficients to be constrained while the underlying system is solved. This favors solutions with reduced sample amplitudes, while relying on redundancies inherent in non-Cartesian sampling patterns to not otherwise affect solution accuracy. When employing this modified linear system with $\lambda=0.55$, it has been shown that the present invention can provide a 28.4 percent increase in SNR and a 10.6 percent reduction in normalized root mean square error (NRMSE) when compared to density-compensated MR images produced using DCF methods such as the Voronoi method. While a wide range of SNR and NRMSE improvements may be provided by the present invention in different imaging systems, such as CT or radio telescopy, it should be noted that excessively high values of $\lambda$ can potentially reverse NRMSE improvements.

It should be recognized that method of the present invention may be employed to exploit similar or additional data set symmetries in related problems, such as rotationally symmetric acquisition patterns in 3D MRI. Furthermore, the method of the present invention may be modified to apply to any set of basis functions and expansion coefficients and can therefore be employed in fields outside of MRI, for example, radio astronomy or computed tomography.

The present invention has been described in accordance with the embodiments shown, and one of ordinary skill in the art will readily recognize that there could be variations to the embodiments, and any variations would be within the spirit and scope of the present invention. Accordingly, many modifications may be made by one of ordinary skill in the art without departing from the spirit and scope of the appended claims.

The invention claimed is:

1. A method for producing density-compensated magnetic resonance (MR) images with a magnetic resonance imaging (MRI) system, the steps comprising;
   a) acquiring MR data using a rotationally symmetric acquisition trajectory;
   b) generating a cross-correlation matrix from the acquired MR data;
   c) applying a Fourier transform (FT) to the acquired MR data and the cross-correlation matrix produced in step b);
   d) computing a set of density-compensated, transformed MR data from the transformed cross-correlation matrix and transformed MR data produced in step c);
   e) applying an inverse FT to the density-compensated, transformed MR data to produce a set of density-compensated MR data; and
   f) performing image reconstruction on the density-compensated MR data to produce a density-compensated MR image.

2. The method as recited in claim 1 wherein the rotationally symmetric acquisition trajectory of step a) is at least one of a periodically rotated overlapping parallel lines with enhanced reconstruction (PROPELLER), BLADE, radial, concentric rings, and spiral trajectory.

3. The method as recited in claim 1 wherein the cross-correlation matrix of step b) has a Toeplitz form.

4. The method as recited in claim 1 wherein step c) further includes applying a discrete Fourier transform (DFT) along a rotationally symmetric dimension and wherein step e) further includes applying an inverse DFT along a rotationally symmetric dimension.

5. The method as recited in claim 1 wherein step d) further includes employing a linear system to compute a set of density-compensated, transformed MR data from the transformed cross-correlation matrix and the transformed MR data.

6. The method as recited in claim 5 further including employing a scaling factor to produce a set of density-compensated, transformed MR data having reduced amplitudes.

7. The method as recited in claim 6 wherein the employment of a scaling factor allows the production of density compensated MR images having an improved signal-to-noise ratio and reduced error.

8. The method as recited in claim 5 wherein the linear system includes a plurality of independent operations configured to be solved in parallel.

9. The method as recited in claim 1 wherein step f) further includes regridding the density-compensated MR data to a Cartesian grid and using a Fourier transform technique to reconstruct the regridded, density-compensated MR data to a density-compensated MR image.

10. The method as recited in claim 1 wherein step f) further includes using a non-uniform Fourier transform technique to reconstruct the density-compensated MR data to a density-compensated MR image.

11. A method for weighting image data to account for non-uniform sampling density and producing a weighted image therefrom, the method comprising the steps of:
   a) acquiring a set of non-uniform image data in a first image space having a non-uniform sampling density;
   b) generating elements of a matrix having a Toeplitz form from the acquired set of image data;

c) transforming the acquired set of image data and the elements of the matrix having the Toeplitz form into a transformed set of image data in a second image space and a transformed matrix in the second image space;

d) weighting the transformed set of image data using the transformed matrix to account for non-uniformity of the sampling density in the set of non-uniform image data and produce a set of transformed and weighted image data in the second image space;

e) transforming the set of transformed and weighted image data to the first image space to produce a set of weighted image data;

f) creating a weighted image from the set of weighted image data; and wherein step b) further includes cross-correlating a plurality of entries in the acquired set of image data to generate the elements of the matrix having a Toeplitz form.

12. The method as recited in claim 11 wherein step a) further includes acquiring the set of image data in the first image space using a rotationally symmetric sampling pattern.

13. The method as recited in claim 12 wherein step a) further includes employing at least one of a computed tomograpy (CT), magnetic resonance imaging (MRI), or radio telescopy system to acquire the set of image data in the first image space.

14. The method as recited in claim 11 wherein:
step c) further includes employing a Fourier transform (FT) to transform the acquired set of image data into transformed set of image data and the elements of the matrix having a Toeplitz form to the transformed set of image data in the second image space and the transformed matrix in the second image space; and step e) further includes employing an inverse FT to transform the set of transformed and weighted MR data to the set of weighted MR data.

15. The method as recited in claim 14 wherein the FT and inverse FT are applied along at least one rotationally symmetric dimension.

16. The method as recited in claim 15 wherein the transformed matrix is a block-diagonalized matrix.

17. The method as recited in claim 11 wherein step d) includes correcting for codependencies between entries in the acquired set of image data.

18. The method as recited in claim 11 wherein step d) further includes employing a linear system to produce the set of transformed and weighted image data.

19. The method as recited in claim 18 wherein a scaling factor is employed to constrain at least one of the amplitude and smoothness of a plurality of entries of the set of transformed and weighted data.

20. The method as recited in claim 11 wherein step f) further includes employing an image reconstruction technique to produce the weighted image.

* * * * *

UNITED STATES PATENT AND TRADEMARK OFFICE
CERTIFICATE OF CORRECTION

PATENT NO.       : 8,473,028 B2
APPLICATION NO.  : 12/743030
DATED            : June 25, 2013
INVENTOR(S)      : Dimitrios Mitsouras et al.

It is certified that error appears in the above-identified patent and that said Letters Patent is hereby corrected as shown below:

In the Specification

Column 2, Line 33, "3°D" should be -- 3D --.

Column 9, Line 30, Eqn. 8:

$$\left[\begin{array}{c}\left(\sum_{\beta=1}^{n}W_{\alpha,\beta}C^{1,\alpha}\right)x^{\wedge\alpha}=b^{\wedge\alpha}\\ \lambda I_{m\times m}\end{array}\right]x^{\wedge\alpha}=\left[\begin{array}{c}b^{\wedge\alpha}\\ 0\end{array}\right]$$

should be $$\left[\begin{array}{c}\left(\sum_{\beta=1}^{n}W_{\alpha,\beta}C^{1,\alpha}\right)x^{\wedge\alpha}=b^{\wedge\alpha}\\ \lambda t_{\alpha\alpha\alpha\alpha} I_{m\times m}\end{array}\right]x^{\wedge\alpha}=\left[\begin{array}{c}b^{\wedge\alpha}\\ 0\end{array}\right]$$

Signed and Sealed this
Thirty-first Day of December, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,473,028 B2  
APPLICATION NO. : 12/743030  
DATED : June 25, 2013  
INVENTOR(S) : Mitsouras et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 454 days.

Signed and Sealed this
Eighth Day of September, 2015

Michelle K. Lee
*Director of the United States Patent and Trademark Office*